(12) United States Patent
Frasch

(10) Patent No.: US 7,161,488 B2
(45) Date of Patent: Jan. 9, 2007

(54) METHOD AND APPARATUS FOR IDENTIFYING INJECTION SYRINGES

(75) Inventor: Eugen Frasch, Oberteuringen (DE)

(73) Assignee: Arzneimittel Gmbh Apotheker Vetter & Co. Ravensburg, Ravensburg (DE)

( * ) Notice: Subject to any disclaimer, the term of this patent is extended or adjusted under 35 U.S.C. 154(b) by 84 days.

(21) Appl. No.: 10/975,925

(22) Filed: Oct. 28, 2004

(65) Prior Publication Data

US 2005/0151652 A1    Jul. 14, 2005

(30) Foreign Application Priority Data

Oct. 29, 2003   (DE) ................. 103 50 422

(51) Int. Cl.
*G08B 13/14*  (2006.01)

(52) U.S. Cl. .............. 340/572.1; 340/571; 340/815.63; 604/404; 604/407

(58) Field of Classification Search .................... None
See application file for complete search history.

(56) References Cited

U.S. PATENT DOCUMENTS

| | | | | |
|---|---|---|---|---|
| 4,853,521 A | * | 8/1989 | Claeys et al. | 235/375 |
| 4,978,335 A | * | 12/1990 | Arthur, III | 604/67 |
| 5,164,575 A | * | 11/1992 | Neeley et al. | 235/472.01 |
| 5,757,021 A | * | 5/1998 | Dewaele | 250/581 |
| 5,772,443 A | * | 6/1998 | Lampotang et al. | 434/272 |
| 5,792,117 A | * | 8/1998 | Brown | 604/207 |
| 5,882,338 A | * | 3/1999 | Gray | 604/131 |
| 6,685,678 B1 | * | 2/2004 | Evans et al. | 604/207 |
| 2001/0017817 A1 | * | 8/2001 | De La Huerga | 368/10 |

\* cited by examiner

*Primary Examiner*—Daniel Wu
*Assistant Examiner*—Son Tang
(74) *Attorney, Agent, or Firm*—Andrew Wilford

(57) ABSTRACT

A method and device for identifying, testing or clearing a prefilled medicinal syringe in which the syringe is inserted into the test device which reads coding on the syringe and has a display as to whether the syringe is appropriate or not.

12 Claims, 4 Drawing Sheets

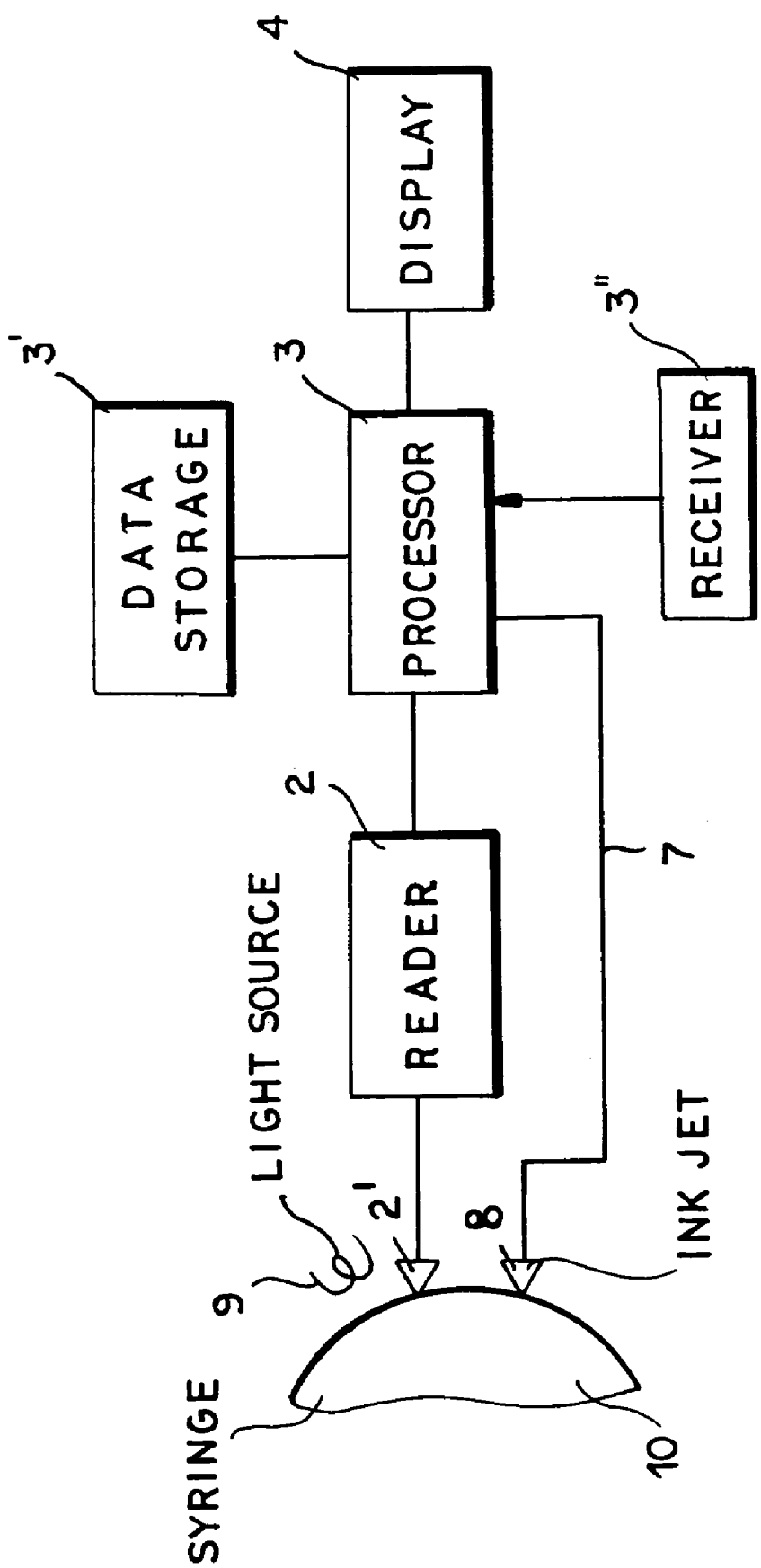

METHOD AND APPARATUS FOR IDENTIFYING INJECTION SYRINGES

FIELD OF THE INVENTION

My present invention relates to a method of identifying and/or testing and/or releasing or clearing for use medicinal syringes, especially prefilled or prepackaged syringes prior to their use for testing such syringes to be certain that the syringe contains the appropriate medication, and for determining applicability of the syringe for a particular treatment by the patient himself or herself. The invention also relates to a test device for carrying out the method.

BACKGROUND OF THE INVENTION

In the current practice of medicine it is not uncommon for injectable, especially intramuscular or subcutaneously administered, medicaments to be prescribed for administration by the patient himself or herself. It is important for such patients to be able to ascertain the applicability of a particular medicinal or pharmaceutical, prepackaged in a syringe for his or her treatment. The identification and/or testing and/or clearance of prefilled medicinal syringes is also important for pharmacists, hospital personnel, care givers and others involved in the chain of distribution and administration of medicinals by syringes.

For the purposes of the invention the syringe will be understood to be provided with some form of machine readable labelling or coding, indicating the contents of the syringe and, preferably, which can be effectively read only if the syringe has not been tampered with, previously used or refilled. For that purpose a device capable of reading the coding on the syringe can serve for the purposes of the invention.

As a general matter, prepackaged medication in the form of a syringe is widely used by diabetics and patients with other ailments and for these patients a similar level of security and reliability that the medication is proper, is required as has been the case for some time for medicaments in the form of drops or tablets. In such cases, the medicament or the package has been color-coded or the tablets have been of particular shapes all designed to assure the patient that he or she is taking the correct medication. That has not been the case up to now where the medicament has been prepackaged in a syringe. True syringes or other packaging have been labelled, but once the packaging material has been removed, it has not generally been possible to reliably determine in rapid manner whether the particular syringe contains a particular medicament, is the proper syringe for administration, etc.

OBJECTS OF THE INVENTION

It is, therefore, the principal object of the present invention to provide a method which can allow coding of a syringe to be read rapidly and accurately and, in particular, the person handling a syringe to reliably determine whether the contents thereof are suitable for a particular application.

It is another object of the invention to provide a method for the purposes mentioned at the outset which can be practiced by the patient himself or herself before self use of a syringe, and particularly to establish the suitability, originality and the freedom from tampering of the contents of a syringe.

Still another object of the invention is to provide a device which can rapidly signal the appropriateness of medication in a syringe for a specific application by a user.

SUMMARY OF THE INVENTION

These objects and others which will become apparent hereinafter are attained, in accordance with the invention in a method in which a syringe is insertable axially into a test device or after such insertion a syringe and the test device are rapidly rotated about common longitudinal axes for the reading of a coding on the syringe by the device, the coding characterizing the contents of the syringe, i.e. containing information as to the medication. That information is compared with stored information and the positive or negative results of that comparison are displayed on the test device to signal to the user whether the contents of the syringe are suitable for the particular treatment or not.

In other words, before the use of a medication containing the coded syringe, the syringe is inserted into the test device, e.g. by the patient himself or herself and the test device signals whether that syringe is suitable for that patient. If the signal is affirmative, the patient can use the syringe. If it is not, the patient will seek a syringe which can pass the test. The signal can be optical and/or acoustic and is, of course, designed to alert especially elderly patients who often have visual or hearing problems to the effect that the syringe may or may not be suitable.

According to a feature of the invention, following the reading of the coding and the testing thereof by comparing it with the stored data, an additional coding is applied to the syringe to indicate that the syringe has already undergone the reading process. This additional coding can be so formed that it permits the use of the syringe after it has undergone one or more readings by one test device but will not permit or approve use when a prior reading has been made by another test device. This, of course, is intended to prevent use of a syringe by another, each test device being possessed by a specific patient, or care giver. This method ensures the originality of a syringe of the particular user and likewise prevents reuse or refilling of a syringe after the medicinal originally therein has been used.

The additional coding may be an imprint applied to the syringe or a modification of a coding previously applied. The application of the additional coding has the advantage that original coding can remain intact and thus details of the manufacturer, charge number and the like remain unaltered. If this is not necessary, the coding following reading can be altered, damaged or destroyed so that a new reading is not possible and the syringe, following its insertion into the test device can no longer be treated as reusable.

To enable the additional coding, if applied, to be readable or detectable in a reliable manner, the reading of the coding is carried out radially and the syringe is rotated through at least 360° so that any additional coding which may have been applied will inevitably fall within the range of the reader. A system in which two rotations are required to ensure full reading of the code where it is radial or peripheral is preferred.

The test device itself may be a cylinder which receives the cylinder or barrel of the syringe. The test device can have a receiving sleeve which is designed to match the barrel or cylinder of the syringe and can be replaceable in the test device so that depending upon the size or nature of the barrel, different adapter sleeves may be used.

Within the interior of the receiving sleeve a reading device can be provided for the coding which can have a two-dimensional or linear optical pickup or sensor response to the coding upon axial displacement of the syringe or rotation of the syringe relative to the sleeve. The device itself may have a data storage for the information received from the reader and for restored information to be compared therewith as well as the indicator unit or display for the results of the comparison.

The test device can be a single unit with a replaceable sleeve or adapter and in that case, simply by replacing the adapter it is possible to match the test device to different syringes. This has been found to be especially advantageous for patients who may require different medications by syringe or a given medicament from syringes of different size.

The adapter can have an optical reading element or lens system as well as any elimination system which may be required for reliable reading of the coding.

As has been mentioned previously, the test device can have a printer which may be manually actuated or automatically actuated to apply the additional coding to the syringe. That printing device may have the form of an ink-jet printing head.

The data syringe can be a part of the test device and/or an external memory module. If the test device contains only a fixed data storage, it usually is correlated with a certain medicament. If an external memory module is provided, it can be a so-called memory stick and the memory module can be distributed by the doctor to the patient, supplied in syringe packaging or otherwise associated with the syringe of a single type. An external module has the advantage that it can be used for a variety of syringes with different medications or different volumes and can store data of other types, for example, for blood sugar determination and can provide information, for example as to insulin dosage or the like.

The indicator can, in a particularly simple arrangement, be a two-color indicator, for example a red/green indicator signalling "no-go" or "go" as to use of the syringe. Alternatively or in addition, it can generate an acoustic output.

The indicator or display unit can also have an α-numeric display which can provide additional information for the patient, for example, a prescribed dosage or the like. The processing circuitry can include a receiver for a time signal transmitter which can supply the actual date and time on a real-time basis, for example to enable the patient to know when it is time to take medications or the like. The coding on the syringe can include prescription data, expiration date data, or the like which may be evaluated in the processor and can provide a basis for displaying an instruction to discard the syringe if necessary.

BRIEF DESCRIPTION OF THE DRAWING

The above and other objects, features, and advantages will become more readily apparent from the following description, reference being made to the accompanying drawing in which:

FIG. 6 is a block diagram of the circuitry which may be part of the device of FIGS. 1 and 4.

SPECIFIC DESCRIPTION

Figure 1:
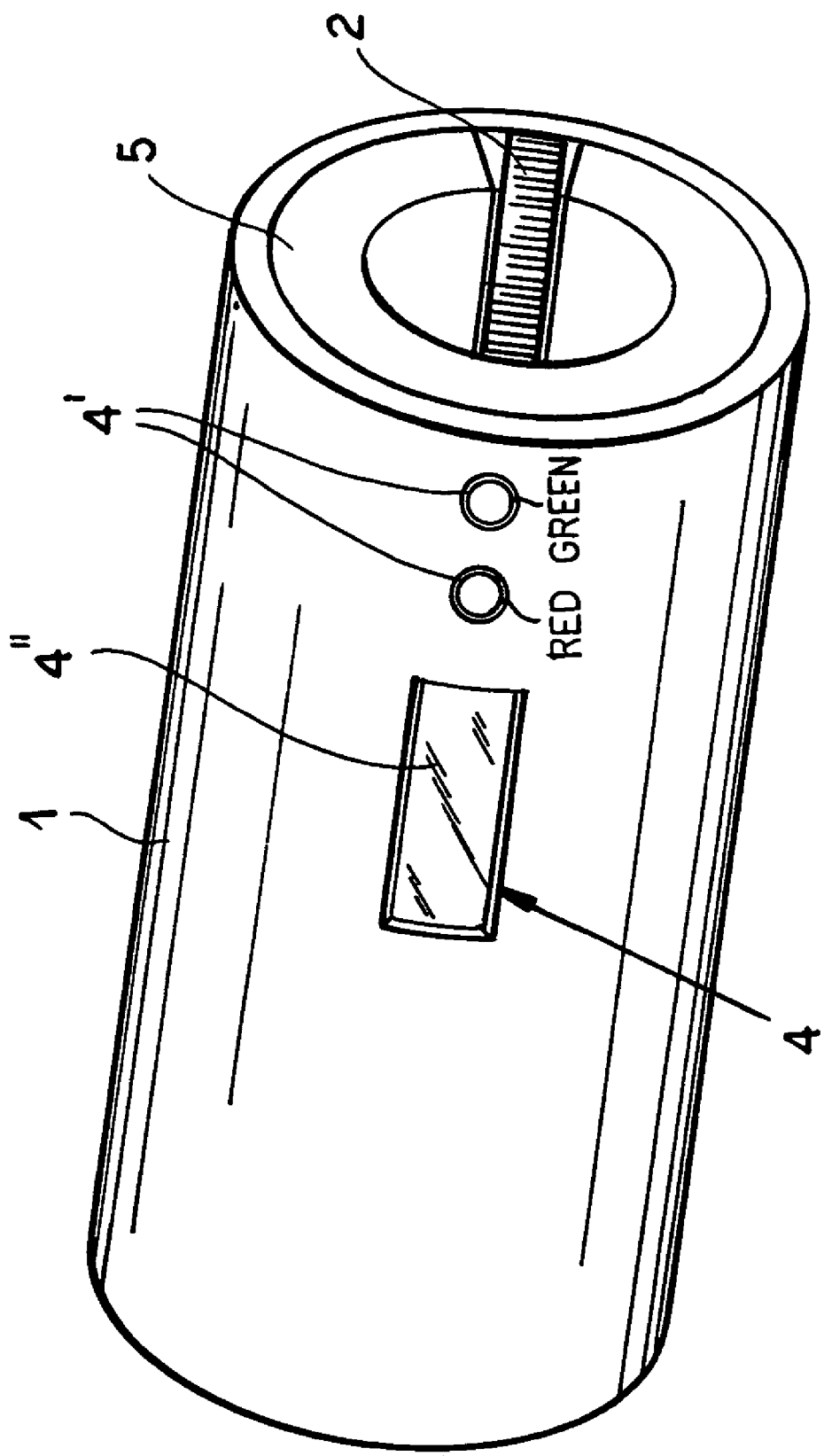
FIG. 1 is a diagrammatic perspective view of a test device according to the invention.
Figure 2:
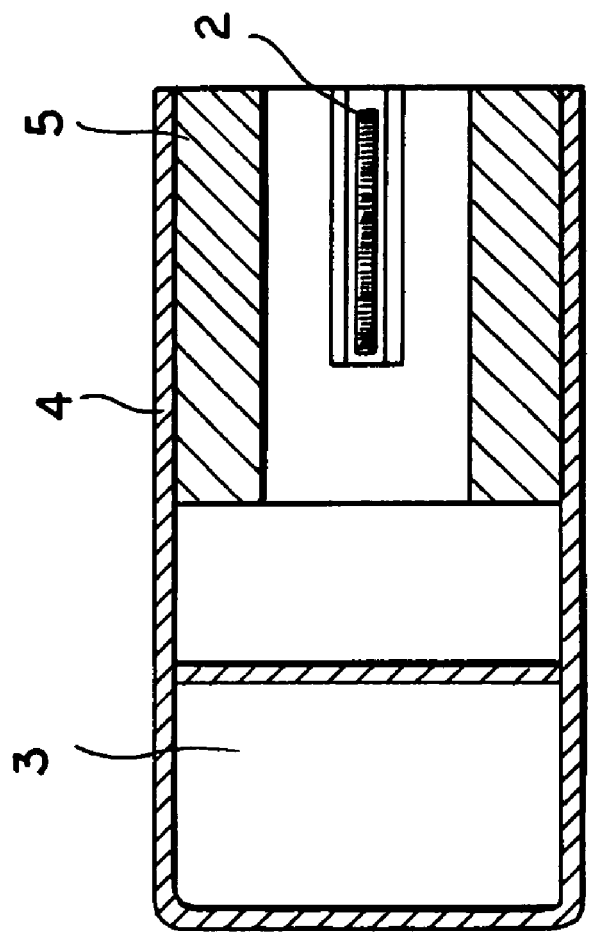
FIG. 2 is a longitudinal section through the test device of FIG. 1 and likewise in highly diagrammatic form.
Figure 3:
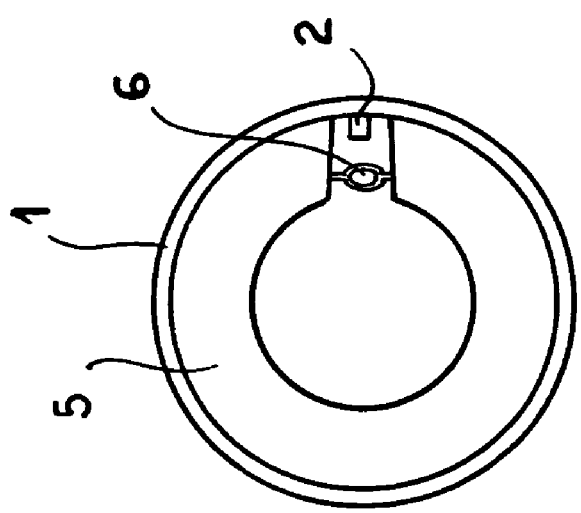
FIG. 3 is a transverse section thereof.
Figures 4, 5:
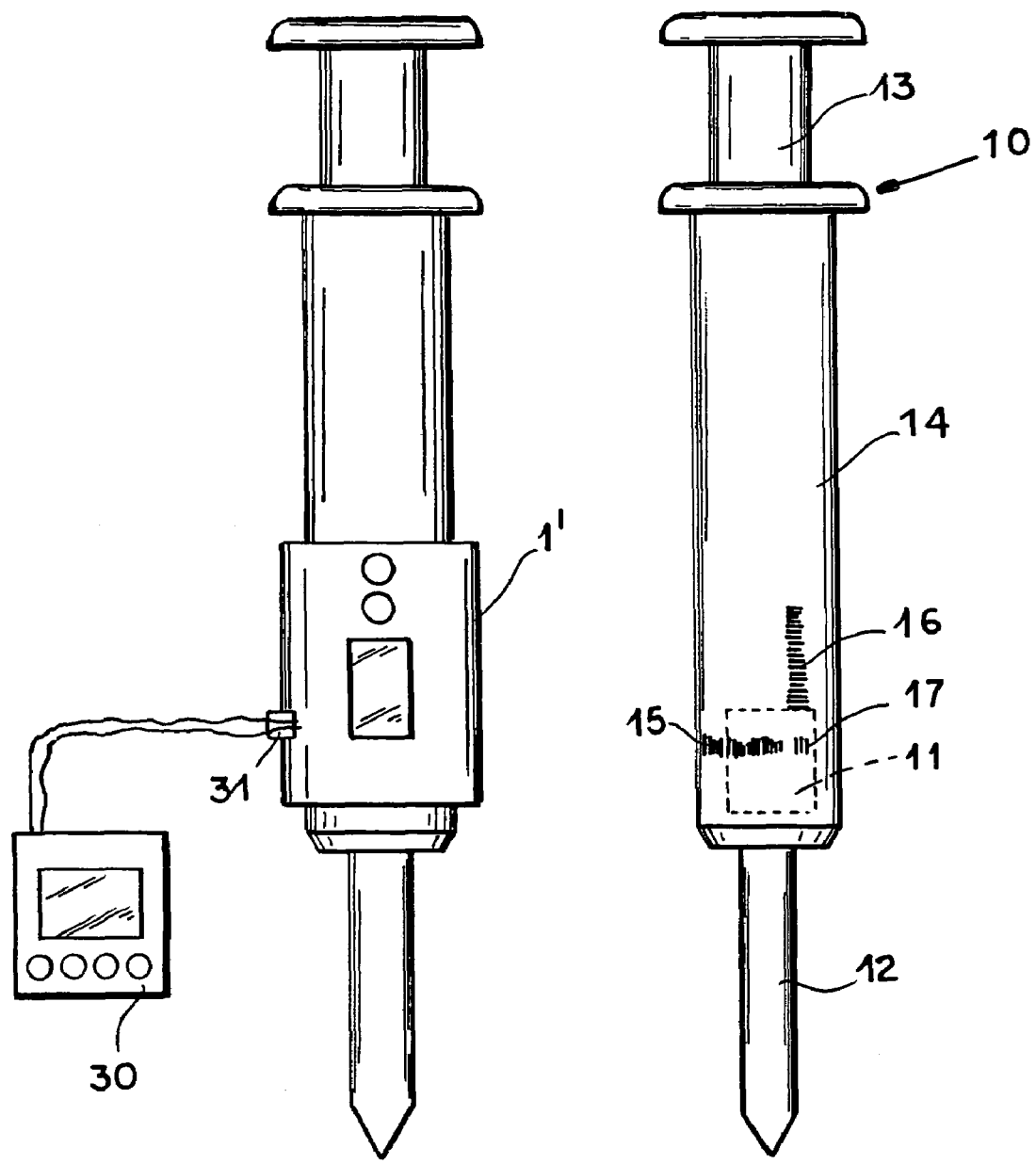
FIG. 4 is a view showing the device as applied to a syringe.
FIG. 5 is an elevational view of a syringe showing linearly and circumferentially arranged coding.

The test device shown in FIGS. 1–3 serves for the reading and testing of a coding on a syringe, for example, the syringe 10 of FIG. 5 which may be prepackaged with a dose of medication at 11 ahead of the needle in its protective sleeve 12 and which can be dispensed when the protective sleeve 12 is removed by depression of the plunger 13. The syringe may have a barrel or cylinder 14 which is provided with the coding 15 in a circumferential pattern or the coding 16 in a linear pattern parallel to the axis and additional coding may be applied as represented at 17 as will be described in greater detail hereinafter.

The test device as shown in FIGS. 1–3 comprises of receiving sleeve 1 in which the coding-carrying part of the syringe cylinder or barrel is received (compare FIG. 4) where the receiving sleeve 1' of a similar test device has been shown. The coding is read by a reader 2 in the interior of the receiving sleeve 1 and which may include a two-dimensional or simpler, e.g. a linear, optical sensor 2. The linear, optical sensor 2 may extend axially along the sleeve 1. When the syringe is inserted into the sleeve it can be rotated to cause the optical sensor 2 to register with the coding 16. Alternatively, the optical sensor may register with the coding 15 and can be read by rotation of the sleeve on the barrel 14 or rotation of the syringe in the sleeve.

If the coding is a radial coding, the syringe is preferably rotated twice to ensure that the coding will be fully read (including any additional coding).

The test unit can also include the processing circuitry 3 with a data storage receiving data from the reader 2 and containing data prestored by means of which the read information can be tested. The test device also includes an indicator 4 for signalling results of the evaluation.

From FIG. 6 it may be seen that the reader circuitry 2 can have an array of sensors 2' and can be connected to a microprocessor 3 to which the data storage 3' is connected and which has an output to the display 4. The processor has a further output at 7 to communicate with the jet printing head 8 for applying the additional coding to the syringe. The light source 9 is trained on the coding on the syringe 10.

To allow the test device to accommodate syringes of different sizes, the receiving sleeve can accommodate any one of a multiplicity of adapters 5 matching the syringes to be tested. The adapters 5 are provided with an optical imaging element for the reader head or 2', which allow the readers to adjust to different syringe diameters and always provide the optimum imaging of the coding on the reader. The light source 9 can likewise be provided in the adapter 5 so that it likewise is accommodated to the configuration of the syringe to be read. The ink jet 8 may also be provided in the adapter so that the position of the ink jet with respect to the barrel in the syringe is always optimum. The data storage can either be a fixed component of the processing circuitry or a separate module as shown at 30 in FIG. 4 as shown at 30 in FIG. 4 with a plug connection 31 to the test device 1' (FIG. 4). In that case the storage module can be used to input various data or used as a display for information with respect to other medicaments, for example for a blood-sugar measuring device. Of course the combination of a fixed and external data storage is also possible. As has been shown in FIG. 1, the indicator 4 can be a two-color indicator 4' with red/green LEDs and/or an α-numeric display 4". Finally, the processor 3 can have a receiving unit 3" for a time signal transmitter and the processor 3 can then compare medication expiration data with real time to signal expiration of a medicament and can provide, through the display, an indication that it is time for the patient to take medication.

I claim:

1. A method of identifying, testing or clearing a prefilled medicinal syringe having a coding thereon indicating the medicinal in said syringe before use of the syringe by a patient, said method comprising the steps of sequentially:
    (a) inserting said syringe into a tubular test device having in an interior thereof a reader for said coding and displacing said syringe relative to said reader rotationally about an axis of the syringe through at least two revolutions, thereby reading any coding on the syringe at least twice;
    (b) comparing the read coding with stored information;
    (c) upon a positive or negative correlation of the read coding and the stored information, generating a signal at an indicator on said test device which represents to a user whether or not the contents of the syringe are usable; and
    (d) printing on the syringe an additional code.

2. The method defined in claim 1 wherein said additional coding is applied to said syringe by modifying the coding originally provided thereon.

3. A test device for identifying, testing or clearing a prefilled medicinal syringe having a coding thereon indicating the medicinal in said syringe before use of the syringe by a patient, said test device comprising:
    a tubular receiving sleeve for receiving a coding-carrying portion of said syringe;
    a reader in the sleeve for said coding having a two-dimensional or linear optical sensor for said coding and extending radially in said sleeve;
    a data storage for information read from said coding by a said reader;
    means for comparing said information with stored information as to contents of a syringe after any coding on the syringe has been read at least twice by the reader; and
    an indicator on said sleeve for, upon a positive or negative correlation of the read coding and the stored information, generating a signal which represents to a user a result of the comparison; and
    a printer in the sleeve for applying an additional coding to the syringe.

4. The test device defined in claim 3 wherein said sleeve has a replaceable adapter matched to a syringe to be tested.

5. The test device defined in claim 4 wherein said test adapted is provided with an optical imaging device for said reader.

6. The test device defined in claim 5 wherein said adapter is provided with an illumination device for said reader.

7. The test device defined in claim 3 wherein said data storage is an integral part of said sleeve.

8. The test device defined in claim 3 wherein said data storage is an external storage module.

9. The test device defined in claim 3 wherein said indicator is a two-color display.

10. The test device defined in claim 9 wherein said indicator is a red/green display.

11. The test device defined in claim 3 wherein said indicator is an alphanumeric display.

12. The test device defined in claim 3, further comprising a processor connected to said data storage and having a receiver for a time signal.

* * * * *